(12) United States Patent
Boukhny et al.

(10) Patent No.: US 7,645,256 B2
(45) Date of Patent: Jan. 12, 2010

(54) ULTRASOUND HANDPIECE

(75) Inventors: Mikhail Boukhny, Laguna Niguel, CA (US); James Y. Chon, Irvine, CA (US); Ahmad Salehi, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 355 days.

(21) Appl. No.: 11/183,591

(22) Filed: Jul. 18, 2005

(65) Prior Publication Data

US 2006/0041220 A1    Feb. 23, 2006

Related U.S. Application Data

(63) Continuation-in-part of application No. 10/916,675, filed on Aug. 12, 2004.

(51) Int. Cl.
*A61B 17/20* (2006.01)
*A61B 17/32* (2006.01)

(52) U.S. Cl. .......................... 604/22; 606/169

(58) Field of Classification Search ............... 600/437, 600/439, 471; 604/22; 606/107, 159, 169, 606/170, 171, 180, 1
See application file for complete search history.

(56) References Cited

U.S. PATENT DOCUMENTS

| | | |
|---|---|---|
| 3,526,219 A | 9/1970 | Balamuth |
| 3,589,363 A | 6/1971 | Banko |
| 3,601,126 A | 8/1971 | Estes et al. |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |

(Continued)

FOREIGN PATENT DOCUMENTS

EP          359217          3/1990

(Continued)

OTHER PUBLICATIONS

Shuyu, Lin. "Sandwiched Piezoelectric Ultrasonic Transducers of Longitudinal-Torsional Compound Vibrational Modes." IEEE Transactions of Ultrasonics, Ferroelectrics and Frequency Control, Nov. 1997, pp. 1189-1197.

(Continued)

*Primary Examiner*—(Jackie) Tan-Uyen T. Ho
*Assistant Examiner*—Dianne Dornbusch
(74) *Attorney, Agent, or Firm*—Kenneth D. Bassinger

(57) ABSTRACT

A handpiece having at least one set of piezoelectric elements polarized to produce longitudinal motion when excited at the relevant resonant frequency. The piezoelectric crystals are connected to an ultrasonic horn to which a cutting tip is attached. The horn and/or the cutting tip contains a plurality of diagonal slits or grooves. The slits or grooves produce optimized torsional movement in the cutting tip when the piezoelectric crystals are excited at a second resonant frequency.

22 Claims, 2 Drawing Sheets

U.S. PATENT DOCUMENTS

| | | |
|---|---|---|
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A | 5/1992 | Ames et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,180,363 A | 1/1993 | Idemoto et al. |
| 5,188,102 A | 2/1993 | Idemoto et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 6,027,515 A | 2/2000 | Cimino |
| 6,028,387 A | 2/2000 | Boukhny |
| 6,077,285 A * | 6/2000 | Boukhny ................... 606/169 |
| 6,083,193 A | 7/2000 | Kadziauskas et al. |
| 6,175,180 B1 | 1/2001 | Angelini et al. |
| 6,179,808 B1 | 1/2001 | Boukhny et al. |
| 6,193,683 B1 | 2/2001 | Ludin et al. |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 | 6/2002 | Boukhny |
| 6,629,948 B2 | 10/2003 | Rockley |
| 6,699,212 B1 | 3/2004 | Kadziauskas |
| 6,780,165 B2 | 8/2004 | Kadziauskas et al. |
| 7,374,552 B2 | 5/2008 | Wuchinich |
| 2001/0001123 A1 | 5/2001 | Madan et al. |
| 2001/0011176 A1 | 8/2001 | Boukhny |
| 2003/0045887 A1* | 3/2003 | Sakurai et al. ............. 606/128 |
| 2003/0164659 A1* | 9/2003 | Iino et al. ............. 310/323.02 |
| 2004/0092800 A1 | 5/2004 | Mackool |
| 2004/0092922 A1 | 5/2004 | Kadziauskas et al. |
| 2006/0041200 A1 | 2/2006 | Dotter et al. |

FOREIGN PATENT DOCUMENTS

| | | |
|---|---|---|
| JP | 09009656 | 10/1997 |
| JP | 2003033364 | 4/2003 |
| WO | 8705793 | 10/1987 |
| WO | WO 92/07622 | 5/1992 |
| WO | WO 99/45868 | 9/1999 |
| WO | WO 01/41672 | 6/2001 |
| WO | WO 2004/080505 | 9/2004 |

OTHER PUBLICATIONS

Jiromaru Tsujino, "Ultrasonic Motor Using A One-Dimensional Longitudinal-Torsional Vibration Converter With Diagonal Slits", Smart Mater. Struct. 7 (1998) 345-351.

* cited by examiner

ULTRASOUND HANDPIECE

This application is a continuation-in-part application of U.S. patent application Ser. No. 10/916,675, filed Aug. 12, 2004, currently co-pending.

BACKGROUND OF THE INVENTION

This invention relates to ultrasonic devices and more particularly to devices for tuning and controlling an ophthalmic phacoemulsification handpiece.

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

There have been prior attempts to combine ultrasonic longitudinal motion of the cutting tip with rotational motion of the tip, see U.S. Pat. No. 5,222,959 (Anis), U.S. Pat. No. 5,722,945 (Anis, et al.) and U.S. Pat. No. 4,504,264 (Kelman), the entire contents of which are incorporated herein by reference. These prior attempts have used electric motors to provide the rotation of the tip which require O-ring or other seals that can fail in addition to the added complexity and possible failure of the motors.

There have also been prior attempts to generate both longitudinal and torsional motion without the use of electric motors. For example, in U.S. Pat. Nos. 6,028,387, 6,077,285 and 6,402,769 (Boukhny), one of the inventors of the current invention, describes a handpiece having two pairs of piezoelectric crystals are used. One pair is polarized to produce longitudinal motion. The other pair is polarized to produce torsional motion. Two separate drive signals are used to drive the two pairs of crystals. In actual practice, making a handpiece using two pairs of crystals resonate in both longitudinal and torsional directions is difficult to achieve. One possible solution, also described by one of the current inventors, is described in U.S. Patent Publication No. US 2001/0011176 A1 (Boukhny). This reference discloses a handpiece have a single set of piezoelectric crystals that produces longitudinal motion, and a series of diagonal slits on the handpiece horn or tip that produce torsional motion when the horn or tip is driven at the resonate frequency of the piezoelectric crystals. Again, in practice, the resonate frequency of the piezoelectric crystals and the tip or horn did not coincide, so simultaneous longitudinal and torsional motion was difficult to achieve.

Accordingly, a need continues to exist for a reliable ultrasonic handpiece that will vibrate both longitudinally and torsionally, either simultaneously or separately.

BRIEF SUMMARY OF THE INVENTION

The present invention improves upon prior art ultrasonic handpieces by providing a handpiece having at least one set of piezoelectric elements polarized to produce longitudinal motion when excited at the relevant resonant frequency. The piezoelectric crystals are connected to an ultrasonic horn to which a cutting tip is attached. The horn and/or the cutting tip contains a plurality of diagonal slits or grooves. The slits or grooves produce optimized torsional movement in the cutting tip when the piezoelectric crystals are excited at a second resonant frequency.

It is accordingly an object of the present invention to provide an ultrasound handpiece having both longitudinal and torsional motion.

It is a further object of the present invention to provide an ultrasound handpiece with a horn having a series of diagonal slits to produce torsional motion.

Other objects, features and advantages of the present invention will become apparent with reference to the drawings, and the following description of the drawings and claims.

DETAILED DESCRIPTION OF THE INVENTION

Figure 2:
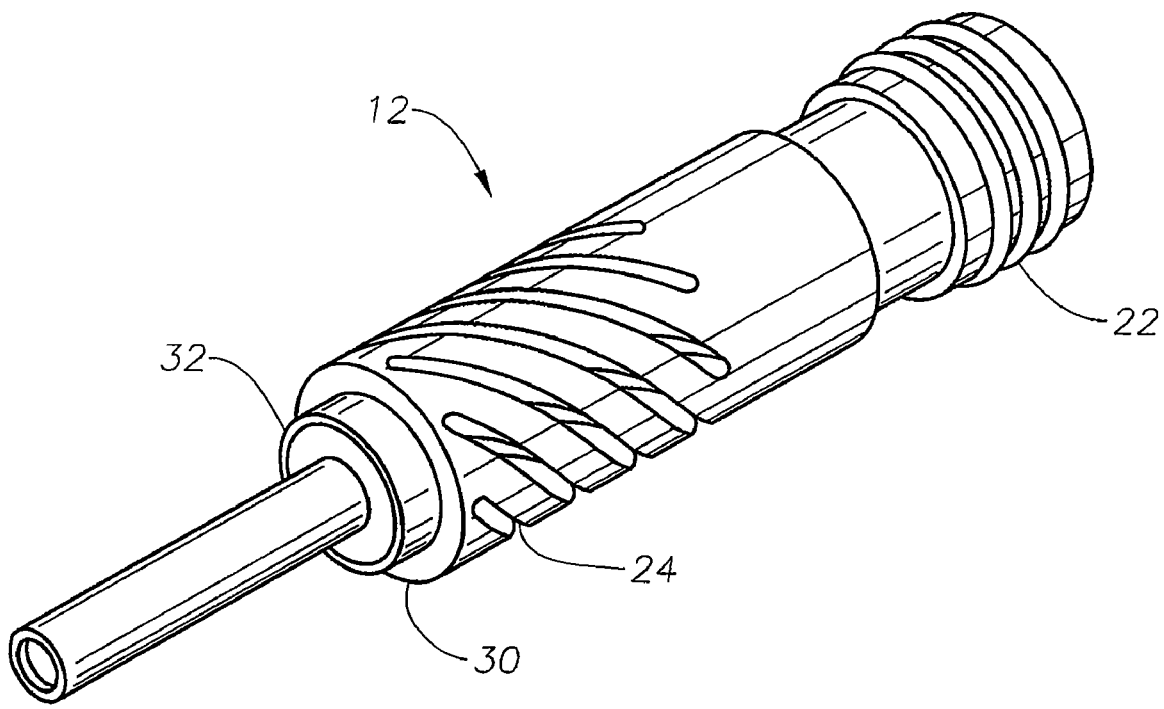
FIG. 2 is a perspective view of the ultrasonic horn that may be used with the handpiece of the present invention.

As best seen in FIG. 2, horn 12 contains a plurality of spiral slits 24. Preferably, the width of slits 24 is between 2% and 65% of the outside diameter of horn 12. This, of course, will affect how many slits 24 can be made on horn 12 (e.g., if slits 24 are 65% of the diameter of horn 12, then only one slit 24 may be cut into horn 12). The width of slits 24 selected will depend upon the desired amount of torsional movement. The depth of slits 24 in horn 12 preferably is between 4% and 45% of the outside diameter of horn 12. Slits 24 may have a flat or square cut bottom, but preferably have a rounded or radiused bottom, which are easier to manufacture. The length of slits 24 preferably is between 8% and 75% of the length of the larger diameter of horn 12. The pitch of slits 24 preferably is between 125% and 500% of the larger diameter of horn 12. By way of example, the inventors have found that one suitable configuration of slits 24 on horn 12 with an outside diameter of 0.475 inches is a total of eight slits 24, having a width of 0.04 inches, a depth of 0.140 (with a full radius bottom), a length of 0.7 inches and a pitch of 1.35 inches gives suitable torsional movement of horn 12 without compromising the longitudinal movement of horn 12.

As best seen in FIG. 2, horn 12 contains a plurality of spiral slits 24. Preferably, the width of slits 24 is between 2% and 65% of the outside diameter of horn 12. This, of course, will affect how many slits 24 can be made on horn 12 (e.g., if slits 24 are 65% of the diameter of horn 12, then only one slit 24 may be cut into horn 12). The width of slits 24 selected will depend upon the desired about of torsional movement. The depth of slits 24 in horn 12 preferably is between 4% and 45% of the outside diameter of horn 12. Slits 24 may have a flat or square cut bottom, but preferably have a rounded or radiused bottom, which are easier to manufacture. The length of slits 24 preferably is between 8% and 75% of the length of the larger diameter of horn 12. The pitch of slits 24 preferably is between 125% and 500% of the larger diameter of horn 12. By way of example, the inventors have found that one suitable configuration of slits 24 on horn 12 with an outside diameter of 0.475 inches is a total of eight slits 24, having a width of 0.04 inches, a depth of 0.140 (with a full radius bottom), a length of 0.7 inches and a pitch of 1.35 inches gives suitable torsional movement of horn 12 without compromising the longitudinal movement of horn 12.

Figure 1:
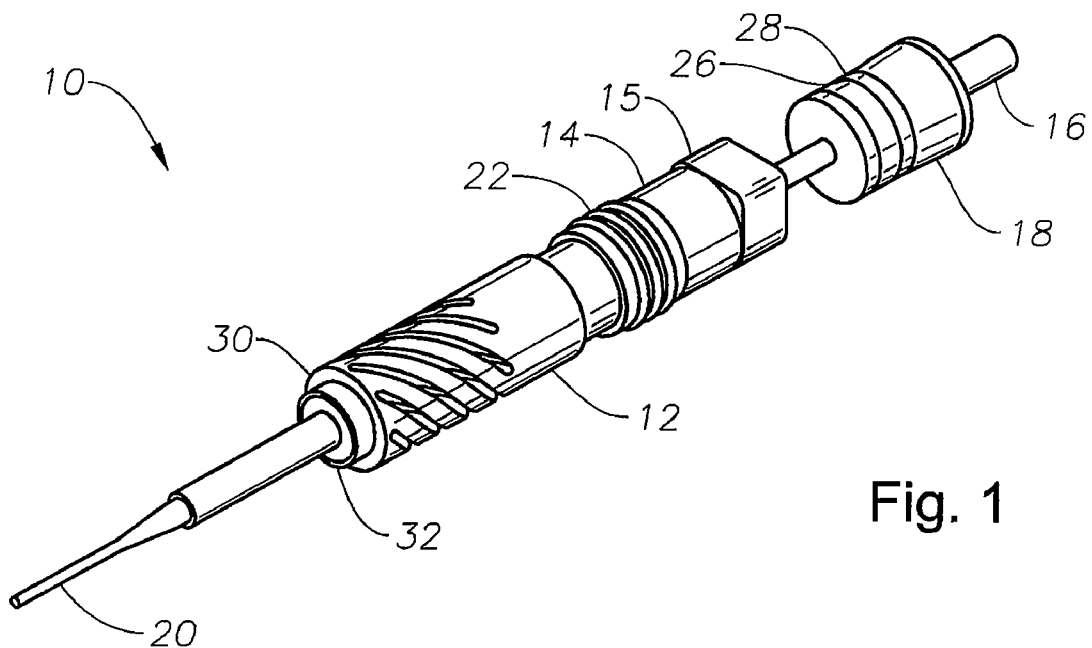
FIG. 1 is a perspective view of the handpiece of the present invention with the outer case removed.

As best seen in FIG. 1, the location of longitudinal and torsional nodal points (the points with zero velocity of the respective mode) is important for proper functioning of handpiece 10. The torsional node 26 preferably is located at the proximal longitudinal node 28, so that the torsional node 26 and the longitudinal node 28 are coincident, e.g., both of which are located on plug 18. Handpiece 10 also contains a distal longitudinal node 30 located at reduced diameter portion 32 of horn 12.

Figure 3:
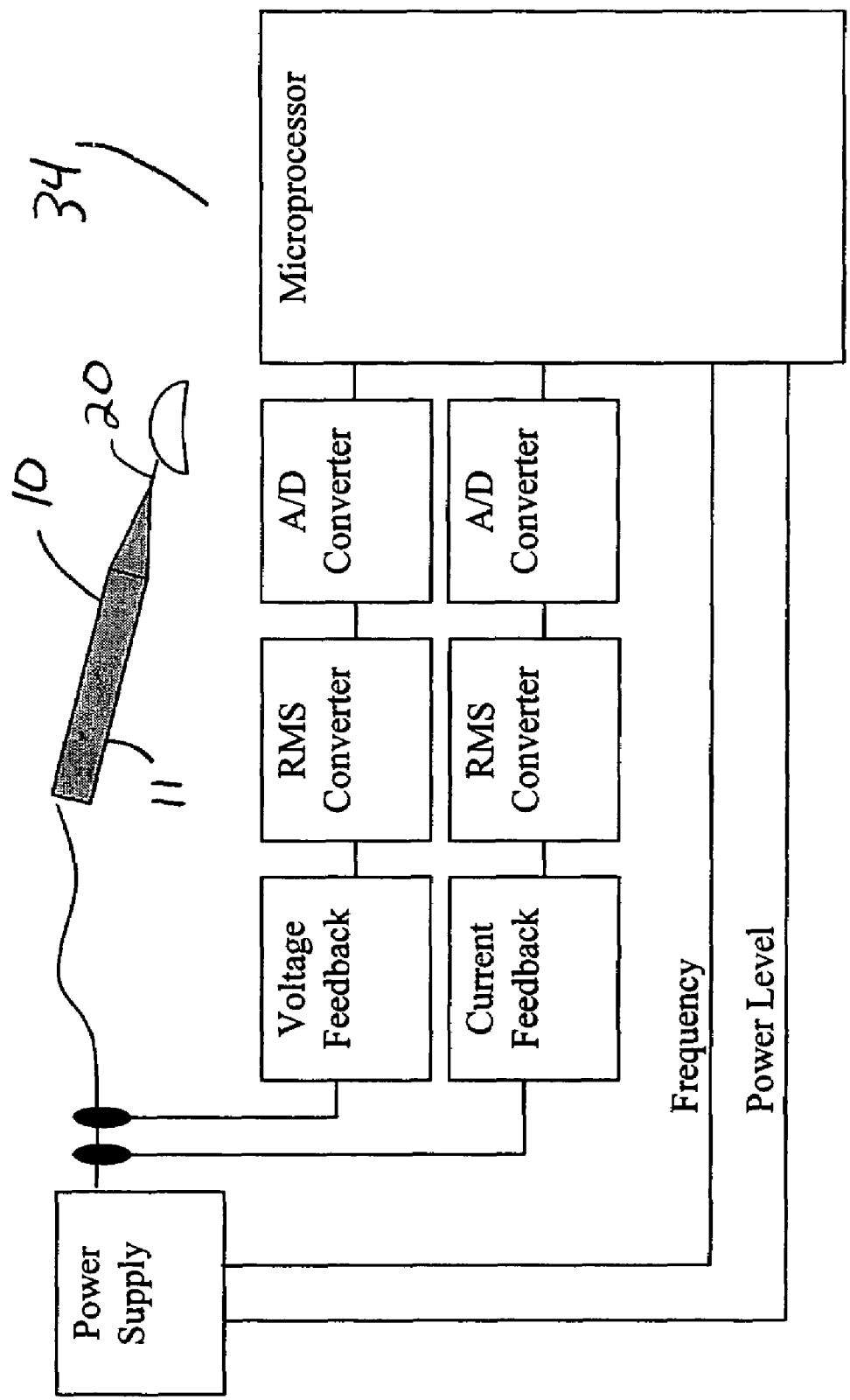
FIG. 3 a block diagram of a driving circuit that may be used with the present invention.

As best seen in FIG. 3, drive circuit 34 that may be used with handpiece 10 of the present invention preferably is similar to that described in U.S. Pat. No. 5,431,664, the entire contents of which being incorporated herein by reference, in that drive circuit 34 tracks admittance of handpiece 10 and controls the frequency of handpiece 10 to maintain a constant admittance. However, drive circuit 34 monitors both the torsional mode and the longitudinal mode and controls these modes in handpiece 10 using two different drive frequencies. Preferably, the torsional drive signal is approximately 32 kHz and the longitudinal drive signal is 44 kHz, but these frequencies will change depending upon the piezoelectric elements 14 used and the size and shape of horn 12 and slits 24. Although both the longitudinal or the torsional drive signal may be supplied in a continuous manner, preferably the longitudinal drive signal and the torsion drive signal are alternated, so that the drive signal is provided in a desired pulse at one frequency and then switched to the other frequency for a similar pulse, with no overlap between the two frequencies, but no gap or pause in the drive signal. Alternative, the drive signal can be operated in a similar manner as described, but short pauses or gaps in the drive signal can be introduced. In addition, the amplitude of the drive signal can be modulated and set independently for each frequency.

The pause or gap between drive signals can serve various purposes. One purpose is to allow for the ultrasound movement of piezoelectric elements 14 and horn 12 to attenuate or stop so that lens fragments can once again be suctioned to tip 20 and an occlusion reestablished, thereby increasing the holding force on the lens fragment. Reestablishing the occlusion will increase cutting efficiency of the following pulse of ultrasound, whether longitudinal or torsional. Another purpose of the pause or gap between drive signals is to allow for the ultrasound movement of piezoelectric elements 14 and horn 12 to attenuate or stop prior to the other (either longitudinal or torsional) mode being excited. Such attenuation between drive signals will reduce amount of potential non-linear interactions in the system which can generate undesirable heat and lead to premature degradation of piezoelectric elements 14 or mechanical failure of the entire assembly.

Alternatively, there can be a slight overlap in the longitudinal and torsional drive signals. The overlap may provide relatively short time intervals when the added action of both torsional and longitudinal displacements results in especially fast rate of lens emulsification, and yet the overlap is short enough to prevent piezoelectric elements 14 from premature degradation or failure of the entire mechanical assembly as a result of excessive stress.

Yet another alternative if to have both longitudinal and torsional drive signals overlap completely thus resulting in applying high stress levels to the lens material when the two signals overlap, and yet leaving a pause in between for the occlusion to reestablish itself and vacuum build-up, thus improving efficiency of the following pulse application.

Still another alternative is to apply a continuous longitudinal signal with a pulsed torsional signal, or vice versa, a continuous torsional signal with a pulsed longitudinal signal. Continuous application of torsional ultrasound does not cause repulsion because tip 20 movement is oriented perpendicular to the direction of the engagement of tip 20 with the lens, and the pulsed applications of longitudinal ultrasound are short enough to prevent overheat or mechanical damage to piezoelectric elements 14.

Finally, as discussed above, both the longitudinal and torsional drive signals can be applied continuously and simultaneously, with the amplitudes of the both signals being selected such that overheating and excessive mechanical stress on the system is reduced. If such a drive scheme is to be used, two sets of piezoelectric elements 14 are preferred with the torsional signal being applied to one set, while longitudinal signal applied to the other set.

While certain embodiments of the present invention have been described above, these descriptions are given for purposes of illustration and explanation. Variations, changes, modifications and departures from the systems and methods disclosed above may be adopted without departure from the scope or spirit of the present invention.

We claim:
1. An ultrasonic handpiece, comprising:
a) a handpiece shell;
b) an ultrasound horn held within the shell; and
c) a plurality of piezoelectric elements connected to the horn, the piezoelectric elements producing torsional movement in the horn in response to a drive signal having a first frequency and a first amplitude and longitudinal movement in the horn in response to a drive signal having a second frequency and a second amplitude;
wherein the drive signal having the first frequency is alternated with the drive signal having the second frequency;

and further wherein the piezoelectric elements and the horn are held within the shell so that a torsional nodal point and a proximal longitudinal nodal point are coincident at a plug that seals the shell on an end of the handpiece opposite a cutting tip.

2. The apparatus of claim 1 wherein the drive signal having the first frequency and the drive signal having the second frequency do not overlap.

3. The apparatus of claim 1 wherein the drive signal having the first frequency and the drive signal having the second frequency overlap.

4. The ultrasonic handpiece of claim 1 wherein the first amplitude and the second amplitude are modulated.

5. An ultrasonic handpiece, comprising:
   a) a handpiece shell;
   b) an ultrasound horn held within the shell; and
   c) a plurality of piezoelectric elements connected to the horn, the piezoelectric elements producing torsional movement in the horn in response to a drive signal having a first frequency and a first amplitude and longitudinal movement in the horn in response to a drive signal having a second frequency and a second amplitude;
   wherein the drive signal having the first frequency is applied continuously and the drive signal having the second frequency is pulsed; and further wherein the piezoelectric elements and the horn are held within the shell so that a torsional nodal point and a proximal longitudinal nodal point are coincident at a plug that seals the shell on an end of the handpiece opposite a cutting tip.

6. The ultrasonic handpiece of claim 5 wherein the first amplitude and the second amplitude are modulated.

7. An ultrasonic handpiece, comprising:
   a) a handpiece shell;
   b) an ultrasound horn held within the shell; and
   c) a plurality of piezoelectric elements connected to the horn, the piezoelectric elements producing torsional movement in the horn in response to a drive signal having a first frequency and a first amplitude and longitudinal movement in the horn in response to a drive signal having a second frequency and a second amplitude;
   wherein the drive signal having the first frequency is pulsed and the drive signal having the second frequency is applied continuously; and further wherein the piezoelectric elements and the horn are held within the shell so that a torsional nodal point and a proximal longitudinal nodal point are coincident at a plug that seals the shell on an end of the handpiece opposite a cutting tip.

8. The ultrasonic handpiece of claim 7 wherein the first amplitude and the second amplitude are modulated.

9. An ultrasonic handpiece, comprising:
   a) a handpiece shell;
   b) an ultrasound horn held within the shell; and
   c) a plurality of piezoelectric elements connected to the horn, the piezoelectric elements producing torsional movement in the horn in response to a drive signal having a first frequency and a first amplitude and longitudinal movement in the horn in response to a drive signal having a second frequency and a second amplitude;
   wherein the drive signal having the first frequency and the drive signal having the second frequency are provided in pulses that overlap completely; and further wherein the piezoelectric elements and the horn are held within the shell so that a torsional nodal point and a proximal longitudinal nodal point are coincident at a plug that seals the shell on an end of the handpiece opposite a cutting tip.

10. The ultrasonic handpiece of claim 9 wherein the first amplitude and the second amplitude are modulated.

11. An ultrasonic handpiece comprising:
    a handpiece shell;
    an ultrasonic horn at least partially located in the shell;
    a piezoelectric element connected to the horn, the piezoelectric element producing torsional movement in the horn in response to a drive signal having a first frequency and longitudinal movement in the horn in response to a drive signal having a second frequency; and
    a plug that seals the shell on an end of the handpiece opposite a cutting tip;
    wherein a torsional nodal point and a longitudinal nodal point are coincident at the plug.

12. The handpiece of claim 11 wherein the drive signal having the first frequency is alternated with the drive signal having the second frequency.

13. The handpiece of claim 11 wherein the drive signal having the first frequency is applied continuously and the drive signal having the second frequency is pulsed.

14. The handpiece of claim 11 wherein the drive signal having the first frequency is pulsed and the drive signal having the second frequency is applied continuously.

15. The handpiece of claim 11 wherein the drive signal having the first frequency and the drive signal having the second frequency are applied continuously.

16. The handpiece of claim 11 wherein the drive signal having the first frequency and the drive signal having the second frequency are provided in pulses that overlap completely.

17. An ultrasonic handpiece comprising:
    a handpiece shell;
    an ultrasonic horn at least partially located in the shell and coupled to the shell at a plug that seals the shell on an end of the handpiece opposite a cutting tip; and
    a piezoelectric element connected to the horn, the piezoelectric element producing torsional movement in the horn in response to a drive signal having a first frequency and longitudinal movement in the horn in response to a drive signal having a second frequency;
    wherein a torsional nodal point and a longitudinal nodal point are coincident at the plug.

18. The handpiece of claim 17 wherein the drive signal having the first frequency is alternated with the drive signal having the second frequency.

19. The handpiece of claim 17 wherein the drive signal having the first frequency is applied continuously and the drive signal having the second frequency is pulsed.

20. The handpiece of claim 17 wherein the drive signal having the first frequency is pulsed and the drive signal having the second frequency is applied continuously.

21. The handpiece of claim 17 wherein the drive signal having the first frequency and the drive signal having the second frequency are applied continuously.

22. The handpiece of claim 17 wherein the drive signal having the first frequency and the drive signal having the second frequency are provided in pulses that overlap completely.

* * * * *

UNITED STATES PATENT AND TRADEMARK OFFICE
CERTIFICATE OF CORRECTION

PATENT NO.      : 7,645,256 B2  
APPLICATION NO. : 11/183591  
DATED           : January 12, 2010  
INVENTOR(S)     : Boukhny et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this

Sixteenth Day of November, 2010

David J. Kappos  
*Director of the United States Patent and Trademark Office*